Aug. 29, 1961 R. S. MOORE Plant Pat. 2,081
MINIATURE ROSE PLANT
Filed Aug. 29, 1960
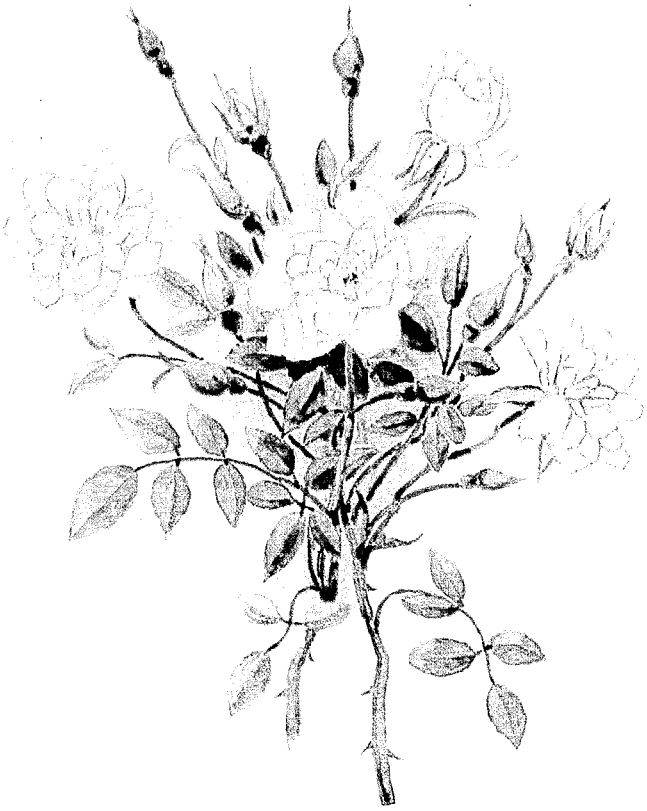
WITNESS
Addison E. Avery
INVENTOR
Ralph S. Moore
Webster & Webster
ATTYS.

United States Patent Office

Plant Pat. 2,081
Patented Aug. 29, 1961

2,081
MINIATURE ROSE PLANT
Ralph S. Moore, Visalia, Calif.
Filed Aug. 29, 1960, Ser. No. 52,752
1 Claim. (Cl. 47—61)

This invention relates to a new and distinct variety of hybrid miniature rose plant of hardy, dwarf, bush type.

The variety is characterized—as to novelty—by a much branched plant which in growing habit resembles a miniature florabunda; by foliage which is slightly larger than that of the average miniature rose but being similar to—although smaller than—the foliage of a hybrid tea rose; by flowers which are a pleasing and unique rose pink color which tends to shade darker, sometimes to a rose red, in cool weather, and in the greenhouse during winter and spring; and by flowers of a form more nearly like those of a hybrid tea rose, and which flowers are borne in clusters or sprays of three to as many as twenty.

In addition to adaptability for growing outdoors and in the greenhouse, the present variety blooms very well as a pot plant.

In comparison, the buds of the present variety of rose plant resemble the Candy Cane (United States Plant Patent No. 1,951) in shape, while the flowers have a general likeness to those of the Polka Dot (unpatented).

The present variety of miniature rose plant was originated by me, in my nursery located at Visalia, California, as a cross between an unnamed red pillar florabunda as the seed parent and Zee as the pollen parent (both unpatented).

Subsequent to origination of the variety I asexually reproduced it, in my nursery located as aforesaid, by budding as well as cuttings; the reproductions having run true in all respects.

The drawing illustrates a spray including foliage, buds, and flowers.

Referring now specifically to the new and distinct variety of miniature rose plant, the following is a detailed description thereof in outline; all major color plate identifications being—as indicated—either by reference to The British Colour Council Horitcultural Colour Chart, or Maerz and Paul Dictionary of Color, except where common terms of color definition are employed.

Type: Hardy; dwarf; bush; seedling; greenhouse; outdoors; cut flowers; garden decoration; pot plant.

Class: Hybrid miniature.

*Flowers*

Continuity: Continuous.

Fragrance: Slight.

Flowers borne: Two to three, sometimes several, to stem, in irregular rounded cluster on strong, medium length stems.

Quantity of bloom: Free, both outdoors and in greenhouse.

Bud:

*Peduncle.*—Medium length; slender to medium; erect; medium green. Numerous green hairs—almost fuzz.

*Before calyx breaks.*—Size—small. Form—pointed; oval; without foliaceous appendages on the surface of the bud, but with tiny short hairs or fuzz; extending beyond the tip of the bud equal to one-half of its length. Color—green.

*As calyx breaks.*—Color—Phlox pink (625/1, British Colour Council).

*As first petal opens.*—Color: outside—Phlox pink (625/1, British Colour Council); inside—Phlox pink (625, British Colour Council). Opening—always opens well.

Bloom:

*Size when fully open.*—Small, averaging 1" to 1½".

*Petalage.*—Double, with from 20 to 40 petals arranged irregularly. During the spring the petals are usually fewer in number (20 to 30), broader, and of deeper color. In the summer the outer petals are large, with a greater number of narrow inner petals; there being very few stamens at such time.

*Form.*—Cupped, high center at first; becoming flat. Petalse remaining at first loosely rolled outward; becoming later at maturity very loosely rolled outward.

Petals: Thick; satiny both inside and outside.

*Shape.*—Outside—obovate, lanceolate. Intermediate—lanceolate. Inside—lanceolate.

*Color.*—Newly opened flower from plant grown outdoors (July)—outside petal: outside surface—Fuchsine pink (627/2); inside surface—Phlox pink (625). Intermediate petal: outside surface—Fuchsine pink (627/1) to Mallow purple (630/1); inside surface—Fuchsine pink (627/1). Inner petal: outside surface—Fuchsine pink (627/1); inside surface—Fuchsine pink (627), or darker; all by reference to British Colour Council. At the basal ends the petals may shade to a greenish-yellow. A flower that was open for three days outdoors (July)—outside petal: outside surface—Fuchsine pink (672/2); inside surface—Fuchsine pink (627/1). Inner petal: outside surface—Fuchsine pink (627/1); inside surface—Fuchsine pink (627/1); all by reference to British Colour Council.

*General color effect.*—Newly opened flower—bright rose-pink. Three days open—bright rose pink, but a slightly lighter shade. Colors fade lighter in very hot weather, but during early spring and in the fall the color deepens, at times, almost to a rose red.

*Behavior.*—Persist for a time.

*Flower longevity.*—Bush in garden (June)—four to five days. Cut flowers kept at living room temperatures (June and October)—three days. Cut flowers grown in greenhouse kept at living room temperatures (March)—four days.

Reproductive organs:

*Stamens.*—Few to medium; arranged irregularly; mixed with petaloids.

*Filaments.*—Short; white or pale yellow.

*Anthers.*—Medium size; open all at once; yellow.

*Pollen.*—Moderate; lemon.

*Pistils.*—Medium number.

*Styles.*—Even; short; medium; bunched.

*Stigma.*—White or greenish-white.

*Ovaries.*—All enclosed in calyx.

*Hips.*—None.

*Sepals.*—Moderate; short; spear shaped; recurved; light green.

*Seeds.*—None.

*Plant*

Foliage:

*Leaves.*—Usually a compound of five leaflets, but sometimes three or seven. Normal abundance; moderately small; leathery.

*Leaflets.*—Shape—lanceloate, with apex acute and base round. Margin—serrate. Color: upper surface—normal green (22–L–9), with young leaves somewhat lighter (21–L–7); under surface—lighter normal green (21–I–6); all by reference to Maerz and Paul Dictionary of Color. Rachis—medium; upper side—grooved, few hairs; under side — moderately thorny. Stipules — medium length; narrow width; with medium length points turning out at an angle of about 45 degrees.

Growth:

*Habit.*—Dwarf; bush; much branched; sometimes of greater width than height.

*Growth.*—Moderate.

*Canes.*—Medium heavy for the type of plant.

*Main stems.*—Color—green. Thorns—color—Linden green (19–J–1), Maerz and Paul Dictionary of Color. Several; medium length; straight, with short oval base. Prickles—none. Hairs—none.

*Branches.*—Color—green. Thorns—several; medium length; very slightly hooked downward, with short base. Prickles—none. Hairs—none.

*New shoots.*—Color—green. Thorns—few; very slightly hooked downward, with short round base. Prickles—none to few. Hairs—none.

The miniature rose plant and its flowers as herein described may vary in slight detail due to climatic and soil conditions under which the variety may be grown; the present description being of the variety as grown at Visalia, California.

The following is claimed:

A new and distinct variety of rose plant of the hybrid miniature class and hardy, dwarf, bush type, characterized by a much branched plant which in growing habit resembles a miniature florabunda, by foliage which is slightly larger than that of the average miniature rose plant but being similar to—although smaller than—the foliage of a hybrid tea rose, by flowers which are a pleasing and unique rose pink color which tends to shade darker, sometimes to a rose red, in cool weather, and in the greenhouse during winter and spring, and by flowers of a form more nearly like those of a hybrid tea rose, and which flowers are borne in clusters or sprays of three to as many as twenty; and further characterized by buds which resemble the Candy Cane in shape, and by flowers having a general likeness to those of the Polka Dot.

No references cited.